(12) United States Patent
Laustsen

(10) Patent No.: US 8,679,778 B2
(45) Date of Patent: Mar. 25, 2014

(54) METHOD FOR PRODUCING A BIOPOLYMER (E.G. POLYPEPTIDE) IN A CONTINUOUS FERMENTATION PROCESS

(75) Inventor: Mads Laustsen, Copenhagen (DK)

(73) Assignee: CMC Biologics A/S, Soeborg, Copenhagen (DK)

( * ) Notice: Subject to any disclaimer, the term of this patent is extended or adjusted under 35 U.S.C. 154(b) by 494 days.

(21) Appl. No.: 12/664,159

(22) PCT Filed: Jun. 11, 2008

(86) PCT No.: PCT/EP2008/057332
§ 371 (c)(1),
(2), (4) Date: Dec. 11, 2009

(87) PCT Pub. No.: WO2008/152075
PCT Pub. Date: Dec. 18, 2008

(65) Prior Publication Data
US 2010/0184149 A1    Jul. 22, 2010

(30) Foreign Application Priority Data

Jun. 13, 2007 (EP) .................................... 07110227

(51) Int. Cl.
*C12P 1/00* (2006.01)
*C12M 1/38* (2006.01)
*C12M 3/00* (2006.01)
*C12M 1/02* (2006.01)

(52) U.S. Cl.
USPC ..... 435/41; 435/286.5; 435/289.1; 435/295.3

(58) Field of Classification Search
USPC ............................ 435/41, 286.5, 289.1, 295.3
See application file for complete search history.

(56) References Cited

U.S. PATENT DOCUMENTS

| 4,806,484 | A | 2/1989 | Petrossian |
| 5,286,646 | A | 2/1994 | Kearns |
| 5,342,781 | A | 8/1994 | Su |
| 6,544,424 | B1 | 4/2003 | Shevitz |
| 2003/0166040 | A1 | 9/2003 | Wilkins et al. |
| 2005/0197496 | A1 * | 9/2005 | Perreault .......................... 530/412 |

FOREIGN PATENT DOCUMENTS

| AU | 82317387 | * | 6/1988 | ............... C12M 1/12 |
| EP | 0270905 | A | 6/1988 | |
| WO | 2005095578 | | 10/2005 | |

OTHER PUBLICATIONS

Alliance Protein Laboratories "Sedimentation Velocity" 6 pages, Available online Feb. 2004.*
Guo et al. "Ultrafiltration and its Applications to Sampling and Characterisation of Aquatic Colloids", Chapter 4 from Environmental Colloids and Particles, 2007, 64 pages.*
Sigma Aldrich "Antibody Basics". 4 pages Accessed online Jul. 9, 2012.*
Follman et al. "Factorial screening of antibody purification processes using three chromatography steps without protein A" Journal of Chromatography A, 1024 (2004) 79-85.*
Millipore "Ultrafiltration Disc Membranes for Stirred Cells and Micropartition System" 10 pages, Jul. 11, 1999.*
Stark et al., "In Situ Product Removal (ISPR) in Whole Cell Biotechnology During the Last Twenty Years" Advances in biochemical Engineering/Biotechnology 2003 vol. 80, 149-175.
Linardos et al., "Monoclonal Antibody Production in Dialyzed Continuous Suspension Culture" Biotechnology and Bioengineering 1992, vol. 39, 504-510.
Poertner et al., "Dialysis cultures" Applied Microbiology and Biotechnology, 1998 vol. 50, 403-414.
Falkenberg et al., "In vitro production of monoclonal antibodies inhigh concentration in a new and easy to handle modular minifermenter", J. Immunol. Methods 179:13-29. 1995.
Examination Report issued in counterpart European Application No. 08774069.2-2401, dated Apr. 26, 2010.
Applicant's reply to Examination Report in European Application No. No. 08774069.2-2401, submitted Oct. 20, 2010.
Notice of intent to grant patent issued in counterpart European Application No. 08774069.2-2401, dated May 27, 2011.
Notice of Opposition to counterpart European Patent No. 217034 filed with the European Patent Office, including the argument and cited references, submitted by opponent on Jul. 26, 2012.
Response to Notice of Opposition to counterpart European Patent No. 2171034, submitted by Application/Proprietor on Oct. 6, 2012.

* cited by examiner

*Primary Examiner* — Thane Underdahl
(74) *Attorney, Agent, or Firm* — Cheryl H. Agris; Agris & Von Natzmer, LLP

(57) ABSTRACT

A method for improving productivity in microbial fermentations and mammalian cell culture bioreactors.

10 Claims, 1 Drawing Sheet

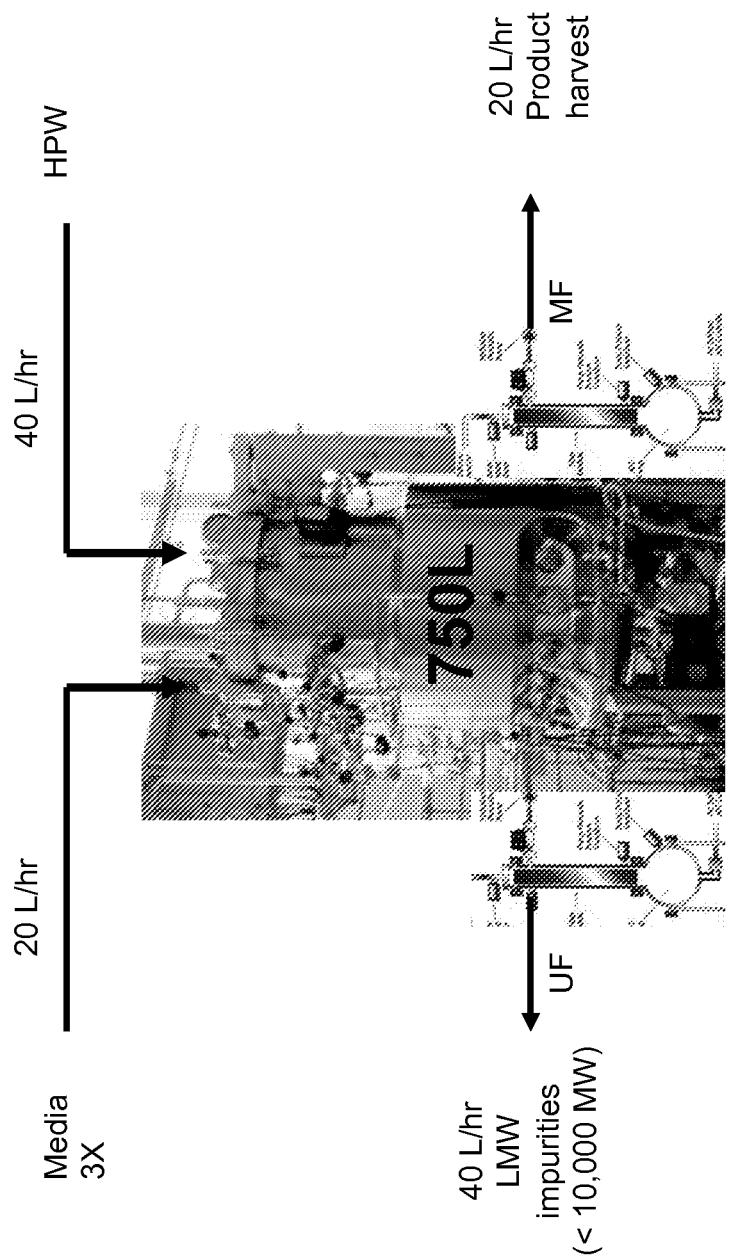

US 8,679,778 B2

METHOD FOR PRODUCING A BIOPOLYMER (E.G. POLYPEPTIDE) IN A CONTINUOUS FERMENTATION PROCESS

CROSS-REFERENCE TO RELATED APPLICATIONS

The present Application is a US national phase of PCT/EP2008/057332 filed on Jun. 11, 2008 ("PCT Application"), which claims priority from European Patent Application No. 07110227.1 filed on Jun. 13, 2007, both of which are hereby incorporated by reference in their entirety into the present Application.

FIELD OF THE INVENTION

The invention relates to a method for improving productivity in microbial fermentations and mammalian cell culture bioreactors.

BACKGROUND OF THE INVENTION

Traditionally, mammalian cells, as well as bacterial cells, are primarily cultured as suspension cultures in bioreactors, which are also, called fermenters. The environmental conditions can be precisely controlled in such vessels. A stirring means moves the culture medium in the interior of the reactor and thus provides for a homogeneous distribution of the cells.

The supply of nutrients to the cells and the removal of waste materials take place, in the case of liquid suspension cultures in bioreactors, according to one of the following processes:

In a batch operation, the reactor is operated discontinuously. At the beginning of a batch, the culture medium usually contains a medium with the necessary nutrients, for example glucose, vitamins, amino acids and minerals. During fermentation, these are consumed so that the medium becomes more and more deprived in nutrients. At the same time, the concentration of waste products increases which finally results in a prevention of the cell growth. The viable cell density achieves a maximum value and thereafter decreases again. Consequently, the culturing is normally discontinued when the maximum cell density is reached or a minimum cell viability is reached. The content of the reactor is then passed on for further downstream processing.

A batch process could be improved by repeatedly refreshing the culture medium without thereby removing cells. However, for this purpose, fresh medium must be added to the cell culture during the fermentation or alternatively a part of the culture medium must be repeatedly removed even though it has by no means been consumed. Such a process is expensive because especially mammalian cell culture medium is difficult to develop and manufacture and consequently is expensive. In this regard the so-called "feedbatch (alternatively named fed-batch) process" is a process in which, during the fermentation procedure, fresh culture medium is not supplied in its totality but only the consumed nutrients are supplied. However, in practice this process does not provide any substantial advantages due to an increase of the waste materials leading to a characteristic course of the cell density during the culturing procedure similar to that in the case of the purely batch process.

The third process is the continuous process. Here, the environmental conditions can be uniformly adjusted so that the cells can grow optimally. However, the process is very laborious and expensive because culture medium must be continuously supplied and removed (with cells and product). Furthermore, in the case of this process too, there is not achieved a substantially higher cell density than in the case of the above-mentioned processes because cells are also continuously removed from the reactor with the running off of cell culture medium.

An example of a special continuous process is the so-called perfusion process. In prior art perfusion culture methods, the waste/impurities in the medium is continuously removed (cells plus product is retained in the bioreactor) from the culture and the displaced medium is replenished with fresh medium. The constant addition of fresh medium and elimination of waste products provides the cells with the environment they require to achieve high cell concentrations and with that higher productivity. Thus, it is possible to achieve a state of equilibrium in which cell concentration and productivity are maintained. Product may be continuously harvested by taking out medium (with cells and product) or via a so-called bleed.

In summary, in a continuous process the bioreactor many times does not comprise a filter that can allow impurities to be removed while retaining cells and high molecular weight compounds (e.g. product) in the bioreactor. In a continuous perfusion process the bioreactor comprises one filter to remove impurities while retaining cells and product or one filter that only retain cell, i.e. both product and impurities pass the filter. Said in other words, the prior art bioreactors comprises only one filter.

U.S. Pat. No. 6,544,424 describes a filtration system for biological fluids creating an alternating tangential flow (ATF) of fluid through a filter element where waste fluids can be removed from the culture by filtration and fresh fluid may be added to replenish the filtered fluid. In the present context this may be seen as an example of a reactor with ONE filter to allow impurities to be removed while retaining cells and high molecular weight compounds (e.g. product) in the bioreactor.

In FIG. 1 herein a prior art reactor may be seen as a reactor with only the UF filter unit to remove impurities or only the filter to remove product and impurities, i.e. a reactor that does not comprise both filters shown in FIG. 1. In other words, the reactor described in e.g. U.S. Pat. No. 6,544,424 lacks the possibility of harvesting high molecular biological products from one filter (product filter) at an adequate out flow speed simultaneously with removing impurities from the culture vessel using a second filter (impurity filter) at an adequate out flow speed.

The following prior art documents:
EP270905A
Stark et al., Advances in biochemical Engineering/Biotechnology 2003 vol. 80, 149-175;
Linardos et al., Biotechnology and Bioengineering 1992, vol. 39, 504-510
Poertner et al., Applied Microbiology and Biotechnology, 1998 vol. 50, 403-414 essentially describes prior bioreactors and impurity removal systems as discussed above and illustrated in FIG. 1—i.e. prior art reactors that lack the possibility of harvesting high molecular biological products from one filter (product filter) at an adequate out flow speed simultaneously with removing impurities from the culture vessel using a second filter (impurity filter) at an adequate out flow speed.

SUMMARY OF THE INVENTION

The problem to be solved by the present invention is to provide a continuous process (e.g. a continuous perfusion process) for increasing productivity of a bioreactor, where productivity of a biopolymer (e.g. a polypeptide) can be improved due to e.g. increased cell density in the reactor and in particular a significant higher concentration of biopolymer of interest in the harvested medium.

The solution is based on that the present inventor has found that by having one membrane based (e.g. ultrafiltration) impurity filter unit and a different product harvest module fitted onto a bioreactor one can get increased cell density in the reactor during a continuous process and in particular one can get a significant higher concentration of biopolymer of interest in the harvested medium. The product harvest module could be a membrane based (e.g. ultrafiltration) filter unit. In such a case the product harvest module is herein termed product filter.

As illustrated in FIG. 1 herein, the solution of the present invention, which relates to a procedure for independently regulating removal of impurities and product harvest is a solution wherein the bioreactor comprises one filter unit to allow impurities to be removed while retaining cells and product in the bioreactor and one product harvest module (e.g. a product filter) to allow product and impurities to be removed while retaining cells in the bioreactor.

The skilled person knows a number of suitable e.g. membrane filters (see below for further details).

In addition, the two independent e.g. filter units may be regulated such that adequate rates of liquid may pass through each filter units thereby reducing harvest volume. This gives the possibility of harvesting high molecular biological products at one adequate flow speed while removing impurities from the culture vessel using a different adequate flow speed and thereby cell density and product yield can be dramatically increased.

This is illustrated in working example 1 and 3 herein. In working example 3 no impurity filter is operating. In step 3 of example 1 is used two filters according to the invention as described herein. One impurity filter and one product filter. This gives a significant improvement as compared to example 3, since one gets an increase in cell density from around 45 mill cells/ml to a cell density of around 60 mill cells/ml and in particular a product accumulation from around 425 mg/L to around 850 mg/L in the harvest stream, when the out flow of media has been separated through two filter units (impurity filter and product filter). Thus, the product gets concentrated from the around 425 mg/L found in the bioreactor in example 3 to around 850 mg/L obtained in the product harvest stream of example 1.

Without being limited to theory it is believed that one reason for one gets an increased cell density in example 1 as compared to the control experiment in example 3 (without use of impurity filter) is that less amount of growth factors, hormones and cytokines such as IGF, hydrocortisone and (re-combinant) insulin are lost from the bioreactor. This is due to that the impurity filter is selected with a pore size such that these compounds cannot easily pass the filter and thus, is held back inside the bioreactor thereby improving the viability of the cells.

The results and conclusions of example 1 to 3 have been confirmed in working examples 4 to 5.

Accordingly, a first aspect of the invention relates to a method for producing a biopolymer of interest in a continuous perfusion fermentation process, wherein the bioreactor comprises an impurity filter unit and a product harvest module characterized by that:
(i) the impurity filter unit allows impurities with a MW below the MW of the biopolymer of interest to be removed while retaining cells and the biopolymer of interest in the bioreactor (termed "impurity filter"); and
(ii) the product harvest module allows biopolymer of interest and impurities to be removed while retaining cells in the bioreactor (termed "product harvest module"); and wherein the method comprises following steps:
(a) fermenting cells expressing the biopolymer of interest in the bioreactor in a suitable medium under suitable conditions;
(b) during the fermentation impurities are removed via the impurity filter;
(c) during the fermentation the biopolymer of interest is harvested via the product harvest module;
(d) during the fermentation is added new medium to replenish nutrients consumed by the cells and to equilibrate the medium removed during step (b) and (c); and
(e) the biopolymer of interest is isolated from the harvested medium; and wherein the cell density in the bioreactor during the fermentation reaches at least 10 million cells per ml medium and wherein impurities are removed via the impurity filter by a flow rate through the impurity filter of step (b) that is at least 25% of the flow rate through the product harvest module of step (c).

DEFINITIONS

Prior to a discussion of the detailed embodiments of the invention is provided a definition of specific terms related to the main aspects and embodiments of the invention. All terms are defined in accordance with the skilled person's normal understanding of the terms.

The term "perfusion" culture of cells refers to that during culturing cells are retained by a separation device (e.g. membrane filter) in which there is an outflow of liquid (comprising e.g. impurities) and in which there is an inflow of the cell culture medium normally through an independent inlet connected to the bioreactor.

Embodiments of the present invention are described below, by way of examples only.

DRAWINGS

FIG. 1: This FIGURE shows an example of a novel bioreactor as described herein. On the left side is an "impurity filter" (UF—remove LMW impurities below 10.000 MW) and on the right side is a "product filter" (MF—Product harvest).

DETAILED DESCRIPTION OF THE INVENTION

Biopolymer of Interest

Biopolymers are a special class of polymers produced by living organisms. Biopolymers, are made of repetitive units called monomers. Biopolymers inherently have a well defined structure: The exact chemical composition and the sequence in which these units are arranged is called the primary structure. Many biopolymers spontaneously fold into characteristic compact shapes, which determine their biological functions. Starch, proteins and peptides, DNA, and RNA are all examples of biopolymers, in which the monomer units, respectively, are sugars, amino acids, and nucleic acids.

In a suitable example the biopolymer of interest has a MW of at least 2,000 kDa, or at least 5,000 kDa, or at least 15,000 kDa, or at least 25,000 kDa or at least 50,000 kDa.

Suitable examples of a biopolymer of interest include a polypeptide, polysaccharide, polypeptide/polysaccharide hybrid, polynucleotide, which are polymers derived from ribonucleic acid (RNA) and deoxyribonucleic acid (DNA), polyhydroxybutyrate a class of polyesters produced by certain bacteria, cis-1,4-polyisoprene the major component of rubber tree latex.

In a preferred embodiment the biopolymer is a polypeptide of interest.

Polypeptide of Interest

In principle any polypeptide of interest may be produced as described herein.

However, in a suitable example the polypeptide of interest has a MW of at least 5.00 kDa, or at least 15,000 kDa, or at least 20,000 kDa or at least 40,000 kDa.

Suitable examples of a polypeptide of interest include an antibody, antibody fragment, Human growth hormone, Follicle-stimulating hormone, Factor VIII, Erythropoietin (EPO), Granulocyte colony-stimulating factor (G-CSF), alpha-glactosidase A, alpha-L-iduronidase (rhIDU; laronidase), N-acetylgalactosamine-4-sulfatase (rhASB; galsulfase), DNAse, Tissue plasminogen activator (TPA), Glucocerebrosidase, Interferon (IF), Insulin, Insulin derivative, Insulin-like growth factor 1, Tenecteplase, antihemophilic factor, human coagulation factor, Etanercept, Trastuzumab, Infliximab, Basiliximab, Daclizumab or Glucocerebrosidase.

Bioreactor

The term "bioreactor" refers to any device or system that supports a biologically active environment. In one case but not limited to, a bioreactor is a vessel in which is carried out a chemical process which involves organisms or biochemically active substances derived from such organisms. This process can either be aerobic or anaerobic. Bioreactors are commonly cylindrical, ranging in size from some litres to cubic meters, and are often made of stainless steel but could also be made of other materials such as disposable materials.

A bioreactor may also refer to a device or system meant to grow cells or tissues in the context of cell culture. On the basis of mode of operation, a bioreactor may be classified as batch, fed-batch or continuous (e.g. continuous stirred-tank reactor model). An example of a bioreactor is the chemostat. The bioreactor may be equipped with one or more inlets for supplying new fresh or concentrated medium to the cells and one or more outlets for harvesting product or emptying the bioreactor. Additionally, the bioreactor may be equipped with at one or more outlets constructed in such a way that filter units can be attached to the bioreactor.

In a preferred embodiment the bioreactor has a volume of at least 50 L, more preferably at least 100 L, even more preferably at least 250 L and most preferably at least 500 L.

Product Harvest Module

A critical element in a culture perfusion system as described herein is the cell/medium separator (herein termed product harvest module). Overall there are two major classes of techniques for the separation of cells from the medium in perfusion bioreactors, namely, by gravitational or centrifugal sedimentation, and by filtration (e.g. tangential filtration such as axial rotation filtration or as spin filters or cross flow filtration).

In an embodiment the product harvest module is a separation device based on gravitational or centrifugal sedimentation. Numerous such sedimentation devices are known in the art (see e.g. U.S. Pat. No. 5,342,781).

In a preferred embodiment the product harvest module is a filter unit. In such a case may herein be termed product filter.

Impurity and Product Filter Units

Several specialized filters and filtration methods have been developed to separate materials according to their chemical and physical properties. Filters, which have been developed in the art, include flat surface filters, pleated filters, multi-unit cassettes, and tubular forms such as hollow fibers. For the invention described herein any system of ultrafiltration technology can be applied as long as sterility can be ensured. Examples of filtration systems applicable for use in the production of polypeptides and removal of impurities as described herein are systems like: cartridge systems, plate and frame and hollow fiber systems. The systems can be operated by pumping of liquid over the membrane, by vibration (like supplied by PallSep) or by alternating tangential flow (ATF) and both polymeric and ceramic membranes are well suited for the filtration process. A skilled person knows to select a membrane with the right properties.

Hollow fiber membranes have been successfully employed in a wide variety of industries including food, juice, pharmaceutical, metalworking, dairy, wine and most recently municipal drinking water. Depending on the application, hollow fiber membranes can be highly practical and cost effective alternatives to conventional chemical and physical separation processes. Hollow fiber membranes offer the unique benefits of high membrane packing densities, sanitary designs and, due to their structural integrity and construction, can withstand permeate back-pressure thus allowing flexibility in system design and operation. Hollow fiber cartridges can operate from the inside to the outside during filtration. This means that process fluid (retentate) flows through the centre of the hollow fiber and permeate passes through the fiber wall to the outside of the membrane fiber. Tangential flow can help limit membrane fouling. Other operating techniques that can be employed with hollow fiber membrane systems include back flushing with permeate and retentate reverse flow.

Accordingly the filter may be located in an external filter module attached to the bioreactor. Alternatively both the impurity filter and the product filter may be located inside the bioreactor. The filter units can also contain pumps or systems for preventing fouling of the filter such as the ATF system described above or the Pallsep system where, controlled horizontal oscillation moves the membrane elements through the feed fluid. The oscillation generates vibrational energy at the membrane surface, giving shear (higher than that typically generated in conventional Tangential Flow Filtration systems) that is limited to a small boundary layer above the membrane surface, and which is not applied to the bulk of the fluid. This ensures that even in high solids feed streams, the membranes do not cake with the retained species. Fluids are processed in a very gentle manner through an open flow path with minimal pressure drop and even transmembrane pressure distribution.

The system can dependant on the metabolites needed to be removed from the process and the product in question be equipped with membranes with a molecular cut off value from a few hundred daltons to tens of thousands. Often membranes with a cut off between 1,000 and 20,000 kDa are used. The benefit of using a membrane with a cut off of 10,000 kDa or preferably around 5,000 Da being that growth factors and Insulin and IGF-1 will be retained in the bioreactor.

Moreover, during an extended run, a filter may be changed and the system resterilized without terminating the fermentation.

The skilled person knows what could be a suitable filter type for removal of impurities and harvest of product and a suitable membrane nominal molecular weight cut-off (NMWC) pore sizes with respect to allowing impurities to perfuse out of the impurity filter and harvest the polypeptide of interest through the product filter.

Nevertheless, the impurity filter is often selected with in within the range of 2.000 to 30,000 NMWC, such as e.g. in the range of 2,000 to 20,000 NMWC or in the range of 2,000 to 15,000 NMWC. Generally speaking it is preferred that the impurity filter has a cut-off of less than 20,000 NMWC).

The product filter is often selected with the range of 50,000 NMWC to 2 μm or 100,000 NMWC to 1 mm.

As know to the skilled person a herein suitable product filter cut off will depend on the size of e.g. the polypeptide of interest. If it is e.g. Erythropoietin (EPO) that has a MW of around 30 kDa then a suitable product filter cut off could be 50,000 NMWC. However, even for a protein such as EPO one would normally use a higher cut off value such as e.g. 500,000 NMWC since at such a cut off value standard production host cells will still be maintained in the media of the bioreactor.

In a preferred embodiment the product filter has a molecular weight cut-off (NMWC) pore size of at least 1.5 times of the MW of the biopolymer (e.g. polypeptide) of interest. For instance if MW of the polypeptide of interest is 100,000 kDa the preferred cut-off of the product filter is at least 150.000 NMWC. Even more preferably, the product filter has a molecular weight cut-off (NMWC) pore size of at least 2 times of the MW of the polypeptide of interest.

In a preferred embodiment the impurity filter has a molecular weight cut-off (NMWC) pore size of a maximum of 80% of the MW of the biopolymer (e.g. polypeptide) of interest. For instance if MW of the polypeptide of interest is 100,000 kDa the preferred maximum cut-off of the impurity filter is 80.000 NMWC. Even more preferably, the impurity filter has a molecular weight cut-off (NMWC) pore size of a maximum of 50% of the MW of the polypeptide of interest.

It may be an advantage that the NMWC of the impurity filter is relatively low if the media comprises useful compounds such as e.g. insulin, which has a MW of around 6 kDa. Accordingly, if e.g. insulin is present in the medium the NMWC of the impurity filter is preferably 10,000 kDa or below In the example illustration in FIG. 1 is the two different e.g. membrane based filter units situated in two physically separated filter support apparatus. It could also be in one filter support apparatus, wherein one could change the membrane filter cut off value according to if it shall be used as impurity filter or product filter in the polypeptide production method as described herein. Preferably, is the two different membrane based filter units situated in two physically separated filter support apparatus.

Fermenting Cells in a Suitable Medium Under Suitable Conditions

The skilled person knows what could be suitable medium and suitable conditions with respect to specific expression cells and polypeptide of interest.

The term "medium" generally refers to, a cell culture medium, which may comprises salts, amino acids, vitamins, lipids, detergents, buffers, growth factors, hormones, cytokines, trace elements and carbohydrates. Examples of salts include magnesium salts, for example $MgCl_2 \times 6H_2O$ and iron salts, for example $FeSO_4 \times 7H_2O$, potassium salts, for example $KH_2PO_4$, KCl; sodium salts, for example $NaH_2PO_4$ or $Na_2HPO_4$ and calcium salts, for example $CaCl_2 \times 2H_2O$. Examples of amino acids are all 20 known proteinogenic amino acids, for example histidine, glutamine, threonine, serine, methionine. Examples of vitamins include: ascorbate, biotin, choline, myo-inositol, and D-panthothenate, riboflavin. Examples of lipids include: fatty acids, for example linoleic acid and oleic acid; soy peptone and ethanol amine. Examples of detergents include Tween 80 and Pluronic F68. An example of a buffer is HEPES. Examples of growth factors/hormones/cytokines include IGF, hydrocortisone and (recombinant) insulin. Examples of trace elements are known to the person skilled in the art and include Zn, Mg and Se. Examples of carbohydrates include glucose, fructose, galactose and pyruvate.

The pH, temperature, dissolved oxygen concentration and osmolarity of the cell culture medium are in principle not critical and depend on the type of cell chosen. Preferably, the pH, temperature, dissolved oxygen concentration and osmolarity are chosen such that it is optimal for the growth and productivity of the cells. The person skilled in the art knows how to find the optimal pH, temperature, dissolved oxygen concentration and osmolarity for the perfusion culturing. Usually, the optimal pH is between 6.6 and 7.6, the optimal temperature between 30 and 39 C, the optimal osmolarity between 260 and 400 mOsm/kg. Alternatively, silicon-based antifoams and defoamers or nonionic surfactants such as coblock polymers of ethylene oxide/propylene oxide monomers may be added to the medium during fermentation. The medium may be water.

The skilled person knows numerous suitable expression cells. In a preferred embodiment, the cell expressing the biopolymer (e.g. polypeptide) of interest is at least one cell selected from the group consisting of *E. coli, Bacillus*, yeast from the genus of *Saccharomyces, Pichia, Aspergillus, Fusarium, Kluyveromyces*, CHO (Chinese Hamster Ovary) cell, hybridomas, BHK (Baby Hamster Kidney) cell, myeloma cell, HEK-293 cell, human lymphoblastoid cell and a mouse cell, for example a NSO cell.

During the Fermentation—Removing Impurities

The term "impurities" shall be understood as the skilled person would understand it in the present context. Impurities are understood as chemical or biological compounds produced by the cells present in the bioreactor, which limit the growth of the cells. Impurities can also arise from cells that die or break open during the fermentation process. Impurities could comprise ethyl alcohol, butyl alcohol, lactic acid, acetone ethanol, gaseous compounds, peptides, lipids, ammonia, aromatic compounds and DNA and RNA fragments.

Isolation of Biopolymer of Interest

According to step (e) of first aspect the biopolymer (e.g. polypeptide) of interest is isolated from the harvested medium. This may be done according to the art.

The reactor may also comprise a so-called bleed where one may take out "whole" medium comprising both polypeptide of interest and cells. This can either be used for further downstream purification of the product of interest or just be discarded. Since the invention as described herein results in high cell density one may advantageously use the media with high cell density to re-start (e.g. seed) a new fermentation.

The isolated biopolymer (e.g. polypeptide) of interest is normally formulated into a final commercial relevant composition of interest (e.g. a pharmaceutical composition of interest). Further it is normally packaged in a suitable container.

Cell Density

Cells that are advantageously subjected to the process of the invention may be any cell type benefiting from this process, i.e. culturing to a high viable cell density.

According to the process of the invention, a high viable cell density is preferably a density of at least 15 mill cells/ml, preferably at least 20 mill cells/ml, more preferably at least 25 mill cells/ml, even more preferably at least 30 mill cells/ml and most preferably at least 50 mill cells/ml.

Regulation of Liquid Flow Rates

In this section there is referred to two filter units. Said in other words a product filter exemplifies the product harvest module. However, a gravitational or centrifugal sedimentation device could as well have exemplified the product harvest module.

In a suitable example the two independent filter units may be regulated such that equal rates of liquid may pass through two filter units. This gives the possibility of concentrating the polypeptide of interest in the bioreactor as compared to a situation in where the bioreactor in operated without an impurity filter (as exemplified by working examples 1 and 3). When cell density increases and thereby also the levels of impurities, perfusion of liquid out through the product filter may be initiated as well as fresh medium may be supplied with the same rate to replenish consumed nutrients and expelled medium.

When the starting criteria for harvest is achieved, the out flow through the impurity filter is also started such that equal rates of medium perfuse out of the impurity filter and the product and the system is readjusted such that fresh medium is feed with the same rate as the sum of the out flow through the impurity filter and the product filter.

This gives a significant improvement in product yield, since the out flow of media is separated through two filter units (impurity filter and product filter) such that the product gets up concentrated with e.g. a factor of two compared to if the product and the impurities would only be harvested through a single filter unit thereby facilitating further down stream processing and the cost involved.

In another appropriate example the two independent filter units may be regulated such that different rates of liquid may pass through each filter units thereby reducing harvest flow. This gives the possibility of harvesting high molecular biological products at one flow speed while removing impurities from the culture vessel using a different flow speed and thereby cell density and product yield can be dramatically increased.

This is illustrated in working example 1 and 2 herein. In step 3 of working example 1 the out liquid flow parameters is adjusted so that 4 L/hr is perfusing out of the impurity filter and 4 L/hr is perfusing as product harvest out of the product filter. In example 2 example 1 is repeated with the only difference that in step 3; 6 L/hr is perfusing out of the impurity filter and 2 L/hr is perfusing as product harvest out of product filter. The result is that the product accumulation in the harvest stream is increased from 850 mg/L to 1250 mg/L.

Accordingly, the impurities are removed via the impurity filter by a flow rate through the impurity filter of step (b) of the first aspect that is at least 25% of the flow rate through the product filter of step (c) of the first aspect.

More preferably, the impurities are removed via the impurity filter by a flow rate through the impurity filter of step (b) of the first aspect that is at least the same as the flow rate through the product filter of step (c) of the first aspect; even more preferably the impurities are removed via the impurity filter by a flow rate through the impurity filter of step (b) of the first aspect that is at least twice the flow rate through the product filter of step (c) of the first aspect.

During the start of the fermentation when the level of product and impurities are low the impurity filter and product filter may be closed such that no liquid pass through the filter units. When cell density increases and thereby also the levels of impurities, perfusion of liquid out through the impurity filter may be initiated as well as fresh medium may be supplied with the same rate to replenish consumed nutrients and expelled medium. The permeate bleed rate and the feed rate may be adjusted accordingly to the level of accumulating impurities When the starting criteria for harvest is achieved, the out flow through the product filter is started and the system is readjusted such that fresh medium is feed with a rate corresponding to the sum of the out flow through the impurity filter and the product filter. In this way, out flow of impurities through the impurity filter may be adjusted according to the rate with which such impurities accumulate. In the same way, out flow of product through the product filter may be adjusted according to the rate with which the product accumulates and consequently, fresh medium is feed with a rate corresponding to the sum of the out flow through the impurity filter and the product filter.

Hence, until the system is stabilized and a steady state is achieved the product accumulates in the bioreactor to lower concentration than when maximum cell density is achieved. Accordingly, it might be beneficial to run the system with a lower out flow rate through the product filter than through the impurity filter such that the product is obtained in a more concentrated solution. In many cases this will facilitate further down stream processing and the cost involved. Another advantage is for example, that unstable polypeptides which may be inactivated or degraded during prolonged time spent in the bioreactor may be harvested already at a low cell density through the product filter at low out flow rate while running the impurity filter at a high out flow rate. Similarly products, which are only expressed to low levels, can also be up-concentrated by the product filter such that the cost of the down stream purification can be optimized significantly.

When the bioreactor is of at least 50 L it is preferred that there in step (d) of the first aspect is added at least 12 L new medium per day which are removed/harvested via the impurity filer and product filter in accordance with step (b) and (c) of the first aspect.

In a number of situations one may advantageously add more new medium such as e.g. at least 1 time the bioreactor volume daily.

EXAMPLES

Example 1

1. A 100 L working volume bioreactor with 50 L of Ex-cell media is inoculated with 15 L of CHO-K1 expressing an IgG antibody.

The system is equipped with an ATF 6 module with a 0.45 micron membrane (product filter) for the product harvest and an ATF 6 module with a 10.000 NMWC membrane (impurity filter) for the low molecular perfusion. After one week of expansion and 5 days of product fermentation the cell density reaches around 15 mill cells/ml in a working volume of 100 L—the starting criteria for use of harvest for downstream processing.

2. The bioreactor is fed with 150 L of media per day to the 100 L working volume and a steady state is obtained after 10 days of harvest with a viable cell concentration of around 30 mill cells/ml and a productivity of around 45 gram antibody per day is obtained. Antibody concentration in the harvest stream is around 300 mg/L. All added media perfuse out through the product filter.

3. At harvest day 10 the ATF 10.000 NMWC is started and the parameters is readjusted so at day 12 8 L/hr (192 L per day) of media is added with 4 L/hr perfusing out of the 10.000 NMWC ATF and 4 L/hr perfusing as product harvest out of the 0.45 micron ATF. At day 20 the system is stabilized at a viable cell density of around 60 mill cells/ml and reached a productivity of around 85 gram per day. The antibody concentration in the harvest is at the same time increased to around 850 mg/L.

The harvest is loaded onto a MabSelect column without any volume or conductivity adjustments with a yield of 90% in the MabSelect eluate to purify IgG antibody.

Conclusion of Results

In step 2 is only used one filter, which is the product filter and one gets a cell density of around 30 mill cells/ml and a product accumulation of around 300 mg/L in the media and thereby in the harvest stream.

In step 3 is used two filters according to the invention as described herein. One impurity filter and one product filter. This gives a significant improvement since one gets a cell density of around 60 mill cells/ml and in particular a product accumulation of around 850 mg/L in the harvest stream, since the out flow of media has been separated through two filter units (impurity filter and product filter) such that the product gets concentrated from the around 300 mg/L found in the bioreactor before the product harvest filter is started to the around 850 mg/L after the product filter is set to operate.

Example 2

Example 1 above is repeated with the only difference that in step 3; 6 L/hr is perfusing out of the 10,000 NMWC ATF and 2 L/hr is perfusing as product harvest out of the 0.45 micron ATF.

The result was that the product accumulation in the harvest stream is increased from around 850 mg/L to around 1250 mg/L by operating the liquid out flow through the impurity filter at three times the rate as the liquid out flow through the product filter.

Example 3

Example 1 above is repeated with the only difference that in step 3 the ATF 10.000 NMWC (impurity filter) is not operating, and all 8 L/hr added media is harvest out of the 0.45 micron ATF (product filter).

At day 20 the system is stabilized at a viable cell density of around 45 mill cells/ml and reached a productivity of around 60 gram per day. The antibody concentration in the harvest is at the same time decreased to around 425 mg/L.

This demonstrates that using the impurity filter in step 3 improved both cell density and product yield.

Example 4

This example was performed essentially as described for example 1 above.

Following was done.

1. A 3.0 L Working volume bioreactor filled with CD-CIM1 media is inoculated with a DG44 CHO cell line expressing an IgG-antibody at an initial viable seed density of 0.5 million cells/ml.

The system is equipped with an ATF 2 module with a 0.2 micron membrane (product filter) and an ATF 2 module with a 10,000 NMWC membrane (impurity filter) for the low molecular perfusion. On Day 2 the viable cell density was 3.0 million cells/ml and perfusate harvest was initiated by both filters.

2. The media feed on the bioreactor is ramped up to 4.5 L of media per day based on maintaining a specific perfusate rate of 0.3 nl/cell*day and a steady state is obtained. 2.25 L of perfusate is removed through the harvest filter and 2.25 L of perfusate is removed through the impurity filter. After 9 days of harvest the viable cell concentration is at 80 million cells/ml and a productivity of 935 mg of antibody per liter bioreactor working volume. Antibody concentration in the harvest stream is 765 mg/L.

Conclusion of Results

The technical conclusions of this example were essentially in agreement with the conclusions of example 1 above.

In step 2 of example 4 two filters are used according to the invention as described herein. One impurity filter and one product filter. This gives a significant improvement since the bioreactor is able to get to a cell density of around 80 mill cells/ml and a product accumulation of 765 mg/L in the harvest stream.

Since the out flow of media has been separated through two filter units (impurity filter and product filter) the product gets concentrated from 260 mg/L found in the harvest stream without the two filter setup (see example 5) to 765 mg/L when two filters was used. Further the cell density was increased from 50 mill cells/ml when only the product filter was used (example 5) to 80 mill cell/ml when both the impurity filter and the product filter was used.

Example 5

Example 4 above is repeated with the only difference that in step 3 the impurity filter was not operated, and all added media was harvested out of the product filter.

Conclusion of Results

The technical conclusions of this example were essentially in agreement with the conclusions of example 3 above.

At day 9 of harvest a viable cell density of 50 mill cells/ml was achieved and reached a productivity of around 525 mg of antibody per liter bioreactor working volume. Compared to example 4, the antibody concentration in the harvest was at the same time only 260 mg/L.

This demonstrates that using the impurity filter in example 4 improved both cell density, productivity and product concentration in harvest.

REFERENCES

1: U.S. Pat. No. 6,544,424
2: EP270905A
3: Stark et al., Advances in biochemical Engineering/Biotechnology 2003 vol. 80, 149-175.
4: Linardos et al., Biotechnology and Bioengineering 1992, vol. 39, 504-510.
5: Poertner et al., Applied Microbiology and Biotechnology, 1998 vol. 50, 403-414.

The invention claimed is:

1. A method for producing a biopolymer of interest in a bioreactor in a continuous perfusion fermentation process, wherein said bioreactor comprises:
  (i) a cell culture vessel which comprises cells that express the biopolymer of interest in a suitable medium;
  (ii) an impurity filter unit, comprising an impurity filter, which allows cell waste and impurities with a molecular weight (MW) below the MW of the biopolymer of interest, to be removed while retaining cells and the biopolymer of interest in the vessel, wherein the biopolymer of interest has a MW of at least 2,000 kDa and the impurity filter has a pore size with a nominal molecular weight cut-off (NMWC) within the range of 1,000 kDa to 15,000 kDa, wherein the impurity filter unit is in fluid communication with the medium inside the vessel (i);
  (iii) a product harvest module, comprising a product filter, wherein the product harvest module allows the biopolymer of interest, cell waste and impurities to be removed from the vessel while retaining cells inside the vessel and wherein the product filter has a pore size with a NMWC within the range of 50,000 kDa to 2 µm, wherein the product harvest module is in fluid communication with the medium inside the vessel (i);

wherein the method comprises following steps:

(a) fermenting cells in the vessel in at least 50 L of suitable medium under suitable conditions which express the biopolymer of interest, wherein the biopolymer of interest has a MW of at least 2,000 kDa, wherein during the fermentation cell waste, impurities and medium are removed via the impurity filter unit, the biopolymer of interest is harvested via the product harvest module and new medium is added to replace the medium removed through the impurity filter unit and the product harvest module; and (b) isolating the biopolymer of interest from the medium from the product harvest module, wherein the cell density in the vessel during the fermentation reaches at least 10 million cells per ml medium; and wherein impurities and cell waste are removed via the impurity filter unit by a flow rate of medium through the impurity filter that is at least 25% of the flow rate of medium through the product filter of step (a).

2. The method of claim 1, wherein impurities and cell waste are removed via the impurity filter unit by a flow rate through the impurity filter of which is at least twice the flow rate through the product filter.

3. The method of claim 1, wherein the biopolymer of interest has a MW of at least 20,000 kDa.

4. The method of claim 1, wherein the biopolymer of interest is an antibody or fragment thereof, Human growth hormone, Follicle-stimulating hormone, Factor VIII, Erythropoietin (EPO), Granulocyte colony-stimulating factor (G-CSF), alpha-glactosidase A, alpha-L-iduronidase (rhIDU; laronidase), N-acetylgalactosamine-4-sulfatase (rhASB; galsulfase), DNAse, Tissue plasminogen activator (TPA), Glucocerebrosidase, Interferon (IF), Insulin, Insulin derivative, Insulin-like growth factor 1, Tenecteplase, antihemophilic factor, human coagulation factor, Etanercept, Trastuzumab, Infliximab, Basiliximab, Daclizumab or Glucocerebrosidase.

5. The method of claim 1, wherein the cell expressing the polypeptide of interest is at least one cell selected from the group consisting of *E. coli, Bacillus*, yeast from the genus of *Saccharomyces, Pichia, Aspergillus, Fusarium, Kluyveromyces*, CHO (Chinese Hamster Ovary) cell, hybridomas, BHK (Baby Hamster Kidney) cell, myeloma cell, HEK-293 cell, human lymphoblastoid cell and a mouse cell.

6. The method of claim 1, wherein there is at least 50 L of medium in the vessel and at least 12 L new medium is added per day which are removed/harvested via the impurity filter and product harvest module in accordance with step (b).

7. The method of claim 1, wherein the isolated biopolymer of interest of step (b) is formulated into a final commercial relevant composition of interest.

8. The method according to claim 1, wherein the cell density in the vessel during the fermentation reaches at least 20 million cells per ml medium.

9. A method for producing a biopolymer of interest in a bioreactor in a continuous perfusion fermentation process, wherein said bioreactor comprises:

(i) a cell culture vessel which comprises cells that express the biopolymer of interest in a suitable medium;

(ii) an impurity filter unit, comprising an impurity filter, which allows cell waste and impurities with a MW below the MW of the biopolymer of interest, to be removed while retaining cells and the biopolymer of interest in the vessel, wherein the impurity filter has a pore size with a NMWC within the range of 2,000 kDa to 30,000 kDa, wherein the impurity filter unit is in fluid communication with the medium inside the vessel (i);

(iii) a product harvest module, comprising a product filter, wherein the product harvest module allows the biopolymer of interest, cell waste and impurities to be removed from the vessel while retaining cells inside the vessel and wherein the product filter has a pore size with a NMWC within the range of 50,000 kDa to 2 µm, wherein the product harvest module is in fluid communication with the medium inside the vessel (i);

wherein the method comprises following steps:

(a) fermenting cells in the vessel in at least 50 L of suitable medium under suitable conditions which express the biopolymer of interest, wherein during the fermentation cell waste, impurities and medium are removed via the impurity filter unit, the biopolymer of interest is harvested via the product harvest module and new medium is added to replace the medium removed through the impurity filter unit and the product harvest module; and (b) isolating the biopolymer of interest from the medium from the product harvest module, wherein the cell density in the vessel during the fermentation reaches at least 10 million cells per ml medium; and wherein impurities and cell waste are removed via the impurity filter unit by a flow rate of medium through the impurity filter that is at least 25% of the flow rate of medium through the product filter of step (a).

10. A method for producing a biopolymer of interest in a bioreactor in a continuous perfusion fermentation process, wherein said bioreactor comprises:

(i) a cell culture vessel which comprises cells that express the biopolymer of interest in a suitable medium;

(ii) an impurity filter unit, comprising an impurity filter, which allows cell waste and impurities with a MW below the MW of the biopolymer of interest, to be removed while retaining cells and the biopolymer of interest in the vessel, wherein the impurity filter has a pore size with a NMWC with a maximum of 80% of the molecular weight of the biopolymer of interest, wherein the impurity filter unit is in fluid communication with the medium inside the vessel (i);

(iii) a product harvest module, comprising a product filter, wherein the product harvest module allows the biopolymer of interest, cell waste and impurities to be removed from the vessel while retaining cells inside the vessel and wherein the product filter has a pore size with a NMWC of at least 1.5 times the molecular weight of the biopolymer of interest, wherein the product harvest module is in fluid communication with the medium inside the vessel (i);

wherein the method comprises following steps:

(a) fermenting cells in the vessel in at least 50 L of suitable medium under suitable conditions which express the biopolymer of interest, wherein during the fermentation cell waste, impurities and medium are removed via the impurity filter unit, the biopolymer of interest is harvested via the product harvest module and new medium is added to replace the medium removed through the impurity filter unit and the product harvest module; and (b) isolating the biopolymer of interest from the medium from the product harvest module, wherein the cell density in the vessel during the fermentation reaches at least 10 million cells per ml medium; and wherein impurities and cell waste are removed via the impurity filter unit by a flow rate of medium through the impurity filter that is at least 25% of the flow rate of medium through the product filter of step (a).

\* \* \* \* \*